US008615410B2

(12) United States Patent
Heeren et al.

(10) Patent No.: US 8,615,410 B2
(45) Date of Patent: Dec. 24, 2013

(54) ONLINE IDENTITY PROOFING USING ELIGIBILITY BASED CRITERIA

(75) Inventors: Andrew Lee Heeren, Olathe, KS (US); Raymond Glen Delano, III, Kansas City, MO (US)

(73) Assignee: Cerner Innovation, Inc., Kansas City, KS (US)

( * ) Notice: Subject to any disclaimer, the term of this patent is extended or adjusted under 35 U.S.C. 154(b) by 405 days.

(21) Appl. No.: 12/979,872

(22) Filed: Dec. 28, 2010

(65) Prior Publication Data
US 2012/0166223 A1 Jun. 28, 2012

(51) Int. Cl.
*G06Q 10/00* (2012.01)
*G06Q 50/00* (2012.01)

(52) U.S. Cl.
USPC .................................. 705/2; 705/3

(58) Field of Classification Search
USPC .......................................... 705/2, 3
See application file for complete search history.

(56) References Cited

U.S. PATENT DOCUMENTS

2007/0106536 A1* 5/2007 Moore ............................. 705/3
2010/0250676 A1* 9/2010 Ufford et al. ................. 709/204

OTHER PUBLICATIONS

Navinet, copyright 2011, whole website, www.navinet.net.
NaviNet New Registration Request Application, 1 page, retrieved Jan. 27, 2011, https://enroll.navimedix.com/enrollment/shared/office-search.

* cited by examiner

*Primary Examiner* — Robert Morgan
*Assistant Examiner* — Maroun Kanaan
(74) *Attorney, Agent, or Firm* — Shook Hardy & Bacon LLP

(57) ABSTRACT

Methods, computer systems and computer readable media for online authentication of an organization are provided. Authentication is accomplished by receiving a first set of patient specific attributes from an organization. This first set of attributes is obtained from an eligibility transaction between the organization and a payor for the patient. The first set of attributes is compared to a second set of attributes involving the same patient, where the second set of attributes is obtained from an eligibility transaction between the online service provider and the payor. If the first set of attributes matches the second set of attributes, the secure online service provider will be notified that the organization is authentic.

14 Claims, 8 Drawing Sheets

1. WELCOME & INTRO ⇨ 2. SECURITY VERIFICATION ⇨ 3. SECURITY CONFIRMATION

WELCOME TO THE INVITATION TOOL! AS AN ENTITY AUTHORITY, YOU WILL HAVE THE CAPABILITY TO ENABLE OTHERS WITHIN YOUR HEALTHCARE ORAGANIZATION(S) LISTED BELOW TO OBTAIN SECURE EMAIL ACCOUNTS ON THE NETWORK. DUE TO THE SECURE NATURE OF THIS NETWORK, IT IS VITALLY IMPORTANT FOR US TO 1.) PROVE THE ORGANIZATION IS LEGITIMATE AND 2.) YOU ARE A VALID REPRESENTATIVE FOR THE SPECIFIED ORGANIZATION BY LEVERAGING STANDARD X12 270 ELIGIBILITY REQUEST AND X12 271 ELIGIBILITY RESPONSE TRANSACTION. THIS IS A QUICK PROCESS AT NO CHARGE TO YOU OR YOUR ORGANIZATION.

YOU HAVE BEEN SELECTED TO BE THE ENTITY AUTHORITY FOR THE FOLLOWING ORGANIZATION(S):

ORGANIZATION NAME                ORGANIZATION NPI#

XYZ HEALTH PROGRAM, INC.         1234567890
310                              312

CONTINUE

IF FOR SOME REASON THE ABOVE INFORMATION IS INCORRECT, PLEASE CONTACT SUPPORT AT DIRECTSUPPORT@COMPANY.COM.

FIG. 3

1. WELCOME & INTRO ⇨ 2. SECURITY VERIFICATION ⇨ 3. SECURITY CONFIRMATION

PLEASE SELECT AN INSURANCE COMPANY FOR ONE OF THE PATIENTS THAT YOU PROVIDED SERVICES FOR TODAY:

<u>WHY IS THIS TYPE OF INFORMATION BEING COLLECTED?</u>

| SELECT ONE ▼ |
| --- |
| PAYOR A |
| PAYOR B |
| PAYOR C |

— 410

IF YOU DO NOT SEE YOUR INSURANCE COMPANY LISTED ABOVE, PLEASE CONTACT SUPPORT AT <u>DIRECTSUPPORT@COMPANY.COM</u>.

1. WELCOME & INTRO ⇨ 2. SECURITY VERIFICATION ⇨ 3. SECURITY CONFIRMATION

PLEASE SELECT AN INSURANCE COMPANY FOR ONE OF THE PATIENTS THAT YOU PROVIDED SERVICES FOR TODAY:

WHY IS THIS TYPE OF INFORMATION BEING COLLECTED?

[PAYOR A ▼] ~510

PLEASE ENTER THE FOLLOWING INFORMATION ON THE PATIENT THAT YOU PROVIDED SERVICES FOR TODAY:

PATIENT'S PROVIDER INFORMATION:
ORGANIZATION NAME [XYZ HEALTH PROGRAM, INC.]   ORGANIZATION NPI# [1234567890]

PATIENT INFORMATION:
PATIENT MEMBER ID [_____] ~512
PATIENT DATE OF BIRTH [ / / ] ~514

PLEASE ENTER THE FIRST 7 DIGITS OF THE ZIP CODE RETURNED BY THE PAYOR FOR THE MAILING ADDRESS OF THE HEALTH PLAN [_____] ~516

PLEASE ENTER THE REMAINING DEDUCTIBLE AMOUNT FOR HEALTH BENEFIT COVERAGE PLAN
$ [____] . [__] ~518

☐ I HEREBY AUTHORIZE A STANDARD X12 270 ELIGIBILITY REQUEST AND X12 271 ELIGIBILITY RESPONSE TRANSACTION
520 (AT NO CHARGE TO MY ORGANIZATION) FOR THE ABOVE PATIENT AND PAYOR FOR THE PURPOSE OF VERIFYING MY ORGANIZATION'S IDENTITY AS A HEALTHCARE SERVICE PROVIDER. THIS INFORMATION IS ONLY USED FOR THE PURPOSE SPECIFIED, AND THE DATA PROVIDED IS NOT RETAINED.

[AGREE & CONTINUE]   [CANCEL]

ONLINE IDENTITY PROOFING USING ELIGIBILITY BASED CRITERIA

BACKGROUND

Identity proofing is a key step to offering healthcare-related services through a secure online network. Identity proofing in the healthcare setting has traditionally been a time-intensive and expensive process requiring face-to-face interactions or interactions over the phone.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

One embodiment of the present invention is directed toward a system that has a receiving component configured to receive identifying information from an organization along with a first set of patient specific attributes from a recent eligibility transaction between the organization and a payor. Along with the receiving component, there is a generating component that generates an eligibility request, and an eligibility request component that is configured to send the eligibility request to the payor to obtain a second set of patient specific attributes. In addition, there is an eligibility response receiving component configured to receive the second set of attributes from the payor, and a matching component configured to compare the first set of attributes with the second set of attributes to determine if they match. As well, the system has a notification component that communicates to a secure online service provider the results of the determination made by the matching component.

Another embodiment comprises a method for online authentication of an organization by using eligibility based criteria. An online authentication system receives a request from an organization for access to a secure online service provider. The online authentication system then receives input data that identifies the organization along with a selection by the organization of a payor, where the selected payor is tied to a patient who recently received services at the organization. Next, the online authentication system receives from the organization a first set of attributes specific to the patient, where the first set of attributes are from data from a standard eligibility transaction between the organization and the payor regarding the patient. An eligibility request to the payor is generated, and a standard eligibility request is run on the patient with the payor to obtain a second set of patient specific attributes. The first set of attributes is compared to the second set of attributes, and it is determined whether the first set of attributes matches the second set of attributes. The results of the determination are then communicated to the secure online service provider.

In yet another embodiment, a graphical user interface (GUI) is provided. The GUI comprises a first display area configured to receive inputs regarding the identity of an organization and a second display area configured to receive a selection of a payor from the organization. A third display area is configured to receive inputs regarding a patient of the selected payor that was seen recently by the organization, with the display area being customized to the selected payor. Next, there is a fourth display area configured to display a success message or a denial message depending on the results of the authentication process.

BRIEF DESCRIPTION OF THE DRAWINGS

Embodiments are described in detail below with reference to the attached drawing figures, wherein:

FIGS. 3-7 are screenshots of graphical user interfaces in accordance with embodiments of the present invention.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" might be used herein to connote different elements of methods employed, the terms should not be interpreted as implying any particular order among or between various steps herein disclosed unless and except when the order of individual steps is explicitly stated.

Embodiments of the present invention are directed to methods, computer systems and computer-readable media for online authentication of an organization in near real-time so that the organization may access a secure online service provider. The organization may wish to take advantage of cloud-based, healthcare-related services and applications provided by a secure online service provider such as secure email, ePrescribing, program/condition management, and other provider-based services. In turn, the secure online service provider wishes to verify that the organization is authentic before allowing the organization access to the secure online healthcare-related services. Online authentication allows for identity proofing to occur in near real-time by leveraging standard eligibility request/response transactions between organizations and payors. This form of identity proofing is much faster than other forms of online identity proofing that rely on data from processed claims. Online authentication allows for savings in both time and money and can be implemented on a national scale.

Online authentication is accomplished by an online authentication service receiving a first set of patient specific attributes from an organization. This first set of attributes is obtained from an eligibility transaction between the organization and a payor for the patient. The first set of attributes is compared to a second set of attributes involving the same patient, where the second set of attributes is obtained from an eligibility transaction between the online authentication system and the payor. If the first set of attributes matches the second set of attributes, the secure online service provider will be notified that the organization, and the person within the organization making the request, is authentic.

Figure 1:
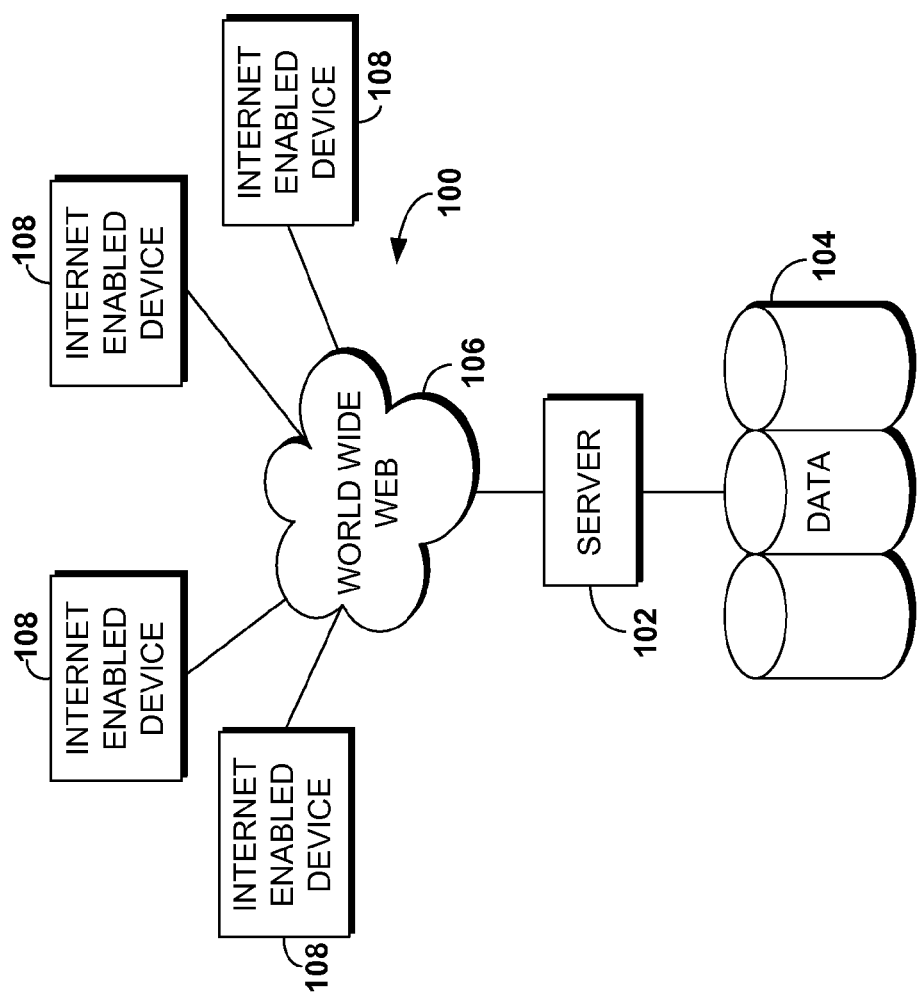
FIG. 1 is a block diagram of an exemplary computing environment suitable to implement embodiments of the present invention.

Having briefly described embodiments of the present invention, an exemplary operating environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. Computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other general purpose or special purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a general purpose computing device in the form of a control server 102. Exemplary components of the control server 102 comprise a processing unit, internal system memory, and a suitable system bus for coupling various system components, including database cluster 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of computer-readable media, for instance, database cluster 104. Computer-readable media can be any available media that might be accessed by control server 102, and includes volatile and nonvolatile media, as well as, removable and nonremovable media. Computer-readable media might include computer storage media. Computer storage media includes volatile and nonvolatile media, as well as removable and nonremovable media implemented in any method or technology for storage of information, such as computer-readable instructions, data structures, program modules, or other data. In this regard, computer storage media might comprise RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 102. Combinations of any of the above also may be included within the scope of computer-readable media.

The computer storage media discussed above and illustrated in FIG. 1, including database cluster 104, provide storage of computer-readable instructions, data structures, program modules, and other data for the control server 102.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and providers' offices. Providers may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. Providers might comprise an entity who meets the definition of a "health care provider" under the Health Insurance Portability and Accountability Act of 1996 (HIPPA). This may comprise any provider of medical or other health services, and any other person or organization that furnishes, bills, or is paid for health care in the normal course of business. The remote computers 108 might also be physically located in nontraditional medical care environments so that the entire healthcare community might be capable of integration on the network. The remote computers 108 might be personal computers, internet enabled devices, servers, routers, network PCs, peer devices, other common network nodes, or the like and might comprise some or all of the elements described above in relation to the control server 102. The devices can be personal digital assistants or other like devices.

Exemplary computer networks 106 comprise local area networks (LANs) and/or wide area networks (WANs) including the World Wide Web. Such networking environments are commonplace in offices, enterprise-wide computer networks, intranets, and the Internet. When utilized in a WAN networking environment, the control server 102 might comprise a modem or other means for establishing communications over the WAN, such as the Internet. In a networked environment, program modules or portions thereof might be stored in association with the control server 102, the database cluster 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, those of ordinary skill in the art will appreciate that such components and their interconnection are well known. Accordingly, additional details concerning the internal construction of the control server 102 and the remote computers 108 are not further disclosed herein.

Figure 2:
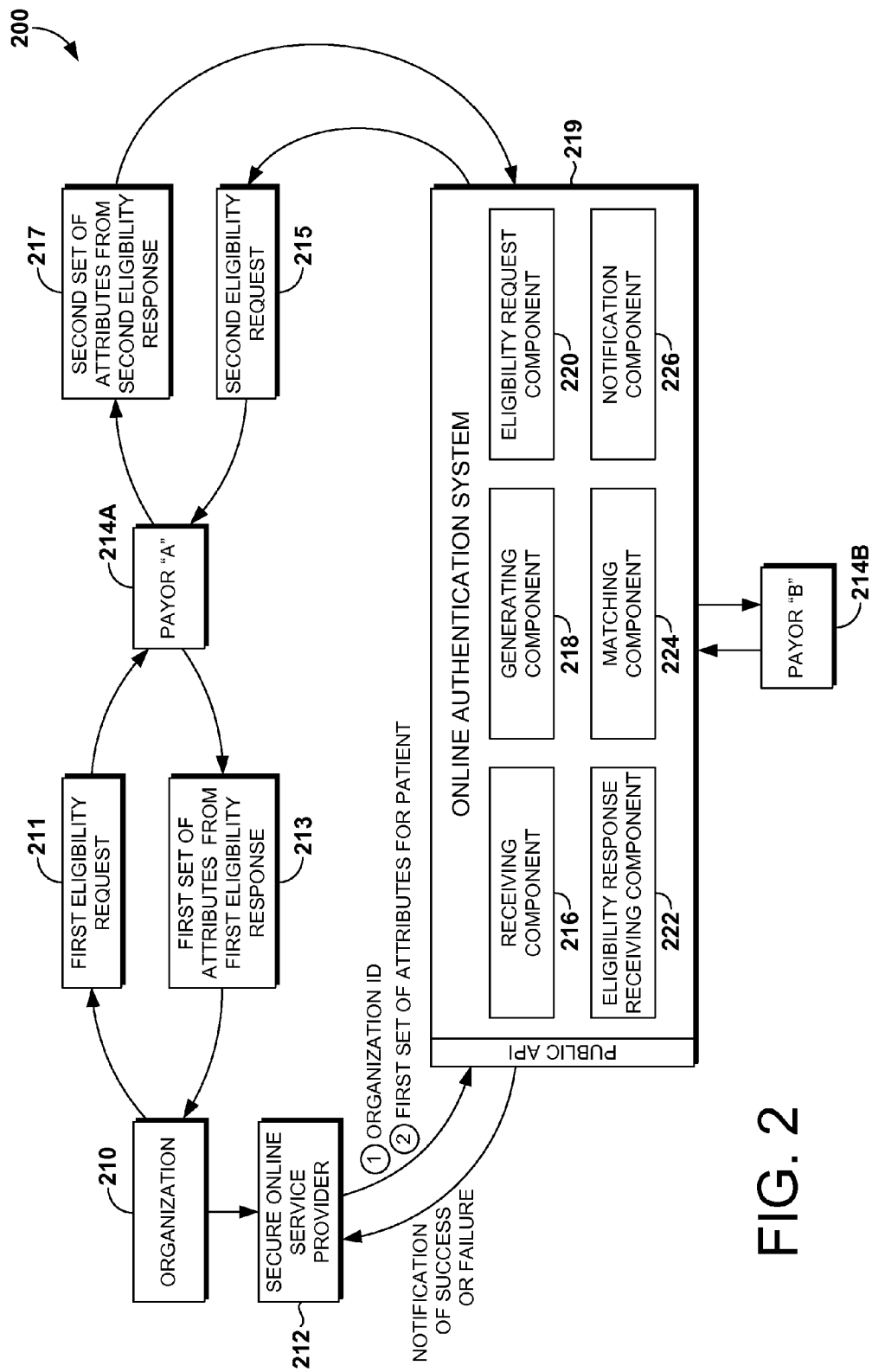
FIG. 2 is an example of system architecture suitable to implement embodiments of the present invention.

Turning now to FIG. 2, a schematic diagram depicts an operating environment, identified generally by reference numeral 200, suitable to practice an embodiment of the present invention. FIG. 2 comprises various components that communicate with one another, including an organization 210, a secure online service provider 212, payor(s) 214, and an online authentication system 219. In turn, online authentication system 219 comprises a receiving component 216, a generating component 218, a eligibility request component 220, a eligibility response receiving component 222, a matching component 224, and a notification component 226.

In an embodiment of the present invention, organization 210 might be any entity that a provider is associated with. For example, organization 210 may comprise inpatient facilities such as hospitals, rehabilitation centers, nursing care facilities, assisted living facilities, and birthing centers. Organization 210 may also comprise outpatient facilities such as ambulatory care facilities, surgical centers, physician offices and clinics. Organization 210 may also comprise health maintenance organizations (HMOs) and preferred provider organizations (PPOs). A provider, in turn, may be any entity who meets the definition of a "health care provider" under the Health Insurance Portability and Accountability Act of 1996 (HIPPA) including any provider of medical or other health services, and any other person or organization that furnishes, bills, or is paid for health care in the normal course of business. In general, health care providers comprise hospitals, nursing homes, ambulatory care facilities, durable equipment suppliers, clinical laboratories, pharmacies, physicians, dentists, psychologists, pharmacists, nurses, chiropractors and other health care practitioners and professionals.

Typically, when a patient is treated or seen by a provider of an organization 210, organization 210 sends a first eligibility request 211 to the payor 214A regarding the patient. Payor 214A may be private insurance companies, employer sponsored programs or state or federally sponsored insurance programs such as Medicaid and Medicare. In one embodiment, first eligibility request 211 may be a standard, HIPPA mandated ASC X12N 270 eligibility request transaction. This transaction is used to acquire information about the eligibility and/or benefits associated with a patient's health plan coverage. The patient is identified as a subscriber or as a dependent. First eligibility request 211 uses information such as the patient's member ID, the patient's first name and last name, the patient's social security number, the patient's date of birth, and such. Typically, first eligibility request 211 is performed in near real-time and contains an inquiry for a single patient. Organization 210 sends first eligibility request 211 to payor 214A through some type of telecommunication and remains connected while payor 214A processes the transaction and returns a response.

After receiving first eligibility request 211 from organization 210, payor 214A returns a first eligibility response 213. In one embodiment, first eligibility response 213 may be a standard, HIPPA mandated ASC X12N 271 eligibility response transaction. First eligibility response 213 may include eligibility status, eligibility begin/end dates, coverage description, and the like. First eligibility response 213 is also a real-time or near real-time transaction and contains information for only the patient that is the subject of first eligibility request 211.

When organization 210 wants to join secure online service provider 212, organization 210 makes a request, and online authentication system 219 receives information identifying the organization along with a first set of attributes 213 from a recent eligibility transaction with payor 214A. Or, alternatively, organization 210 is sent a link by secure online service provider 212, and organization 210 initiates the link and sends the information outlined above to online authentication system 219. In one aspect, online authentication system 219 comprises a public application provider interface. Continuing, the information sent by organization 210 is received by receiving component 216. In one embodiment, the information identifying organization 210 is the organization's name and National Provider Identifier (NPI). The NPI is a standard unique health identifier for health care providers to carry out a requirement in HIPPA for the adoption of such a standard. First set of attributes 213 comprises information from first eligibility request 211 and first eligibility response 213 between organization 210 and payor 214A. First set of attributes 213 received by receiving component 216 may comprise by way of example, but not limitation, such information as the patient's first name and last name, the patient's social security number, the patient's subscriber member ID, the patient's date of birth, the zip code returned by the payor for the mailing address of the payor, the zip code returned by the payor for the mailing address of the patient, the remaining deductible amount for the health benefit plan coverage, and the identity of the payor. The information contained in the first set of attributes may vary depending upon the identity of payor. For example, payor 214A may return the first seven digits of the zip code for the mailing address of the patient, while payor 214B may return the first seven digits of the zip code for the mailing address of the health plan. This variability of information based upon the identity of the payor may be one basis for authenticating the organization.

Generating component 218 of online authentication service 219 generates a second eligibility request 215 for the patient that was the subject of the initial eligibility request/response transaction between organization 210 and payor 214A. In one embodiment of the invention, generating component 218 generates second eligibility request 215 after online authentication service 219 receives permission from organization 210 to perform an eligibility request for the specified patient.

Eligibility request component 220 sends second eligibility request 215 to payor 214A for the patient that was the subject of the initial eligibility request/response transaction between organization 210 and payor 214A. In one embodiment, second eligibility request 215 may be part of a standard, HIPPA mandated ASC X12N 270 eligibility request transaction as described above.

Eligibility response receiving component 222 then receives the results of the second eligibility transaction from payor 214A. The results include a second set of attributes 217 for the patient and information obtained from, for example, a standard, HIPPA mandated ASC X12N 271 eligibility response transaction as outlined above.

Matching component 224 compares first set of attributes 213 with second set of attributes 217 to determine if they match. By way of illustrative example, and not by limitation, a match may be determined if the patient name, zip code, and deductible amount from first set of attributes 213 matches the patient name, zip code, and deductible amount from second set of attributes 217. Notification component 226 notifies secure online service provider 212 of the success or failure of the authentication process. In one aspect, notification component 226 could be in the form of a display component (not shown).

Turning now to FIG. 3, an illustrative graphical user interface (GUI) 300 is shown in accordance with an embodiment of the present invention. GUI 300 is configured to receive inputs regarding the identity of an organization. In one embodiment of the invention, GUI 300 includes an input field for the organization's name 310 and the National Provider Identifier (NPI) 312 associated with the organization. In another embodiment of the invention, the input fields in GUI 300 may be pre-populated by a secure online service provide as explained more fully below.

With respect to FIG. 4, an illustrative graphical user interface (GUI) 400 is shown in accordance with an embodiment of the present invention. GUI 400 is configured to receive a selection of a payor 410 from the organization. The payor may comprise private insurance companies, employer sponsored programs, or state or federally sponsored insurance programs such as Medicaid and Medicare. In one embodiment, the organization is able to input a payor of its choice. Alternatively, the organization selects a payor from a pre-defined list. Still further, in another embodiment of GUI 400, the display area displays which payor the organization is required to use.

FIG. 5 is an illustrative graphical user interface (GUI) 500 in accordance with an embodiment of the present invention. GUI 500 is configured to receive inputs regarding a patient of the selected payor that was seen recently by the organization. GUI 500 is customized to the selected payor. In the example shown, GUI 500 is configured to receive a first set of attributes corresponding to the payor shown in display field 510 (Payor A). This data comprises patient member ID 512, patient date of birth 514, the first seven digits of the zip code returned by the payor for the mailing address of the health plan 516, and the remaining deductible amount for the health benefit coverage plan 518. GUI 500 also has an area 520 where the organization can grant authorization to the online authentication service to run an eligibility transaction on the patient.

Figure 6:
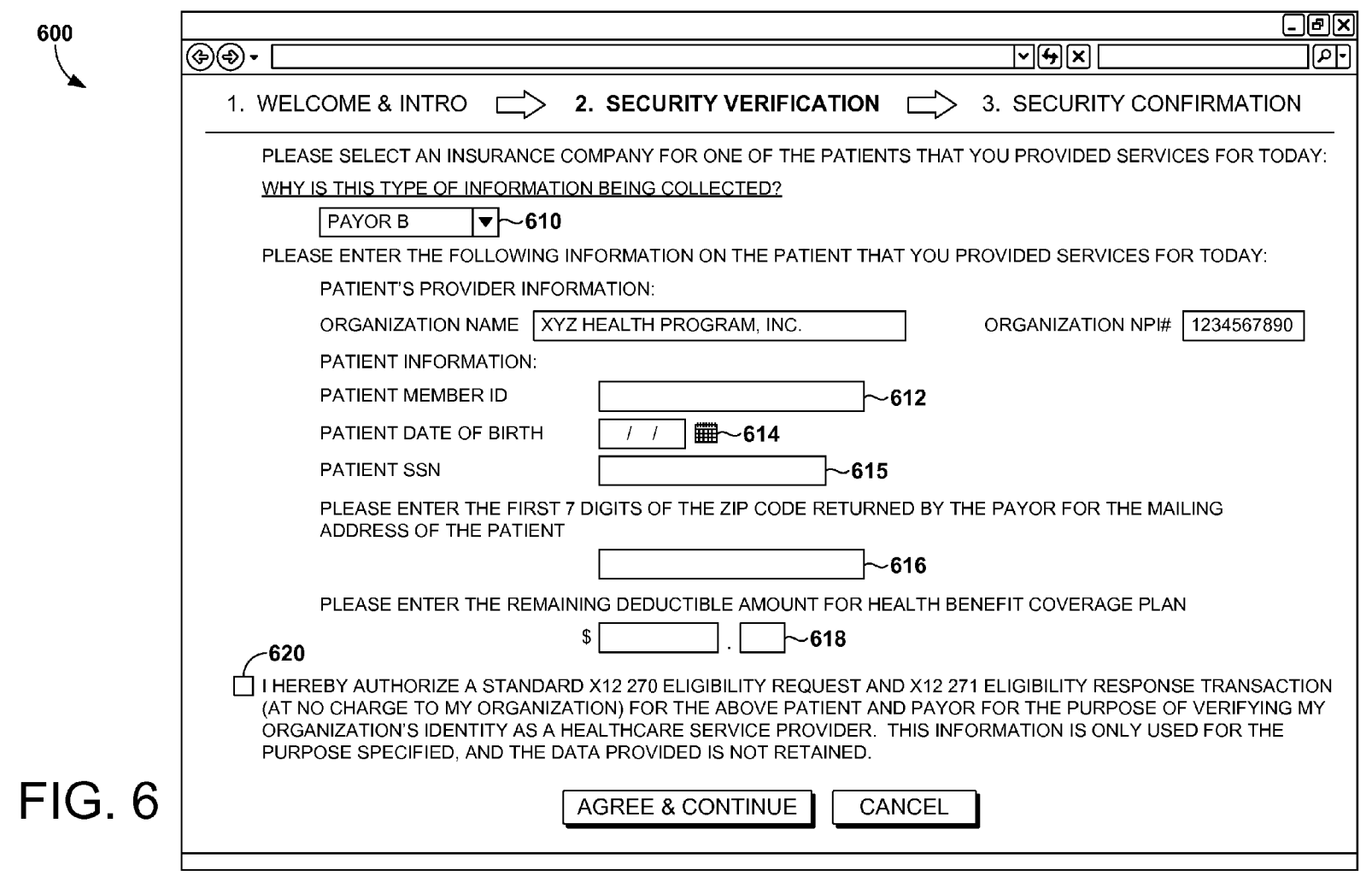

FIG. 6 is an illustrative graphical user interface (GUI) 600 designed to illustrate how the display area is customized to the selected payor. In GUI 600, input field 610 indicates that a different payor has been selected (Payor B). Input fields 612, 614, 618, and 620 correspond to input fields 512, 514, 518, and 520 of GUI 500, but input field 616 is configured to receive the first seven digits of the zip code returned by the payor for the mailing address of the patient. As well, input field 615 is configured to receive the patient's social security number. It is to be understood that there may be a multitude of different GUIs of this type depending on which payor is used.

Figure 7:
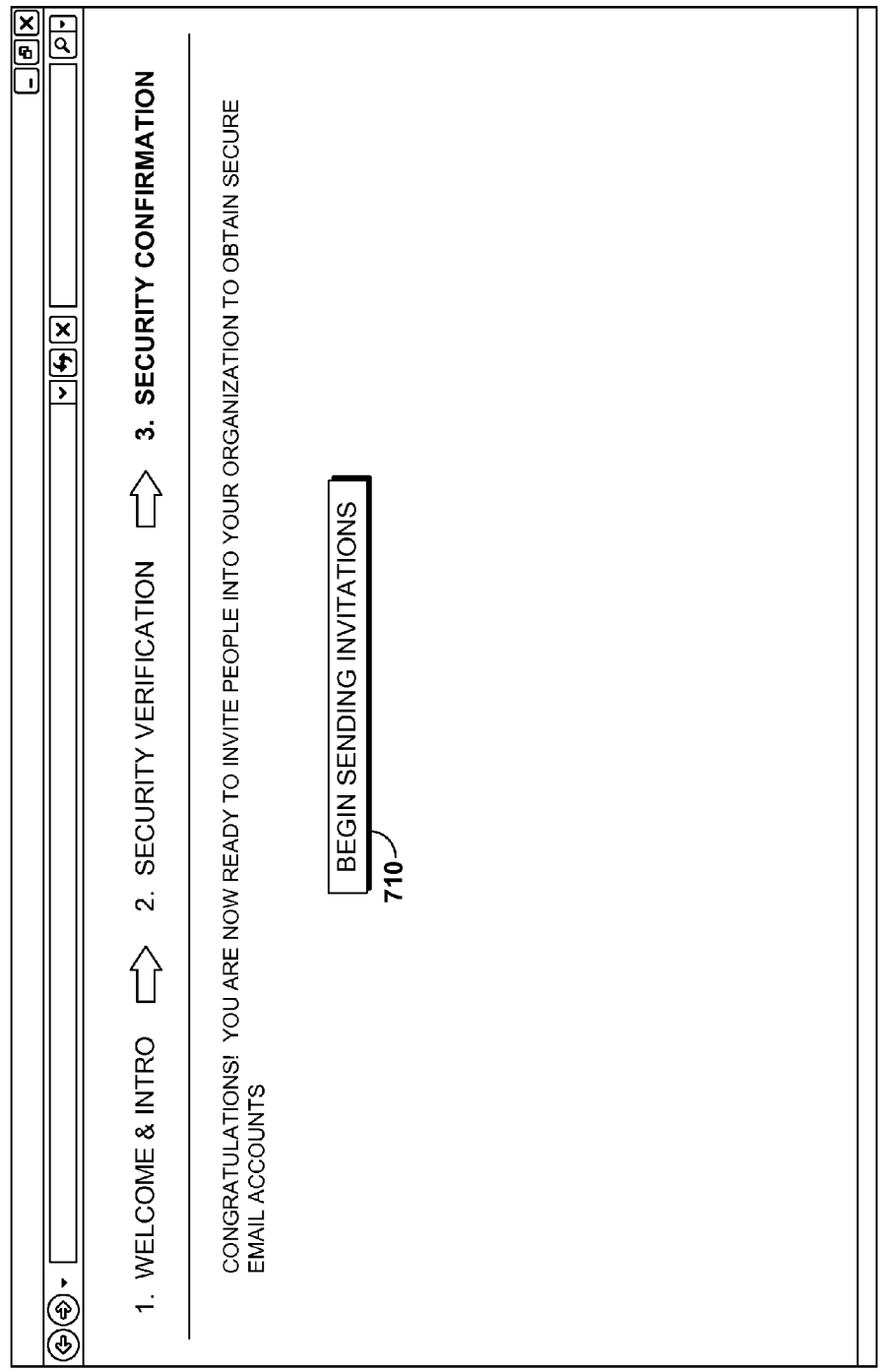

FIG. 7 is a graphical user interface (GUI) 700 of an embodiment of the present invention. GUI 700 is configured to display a success message 710 if it is determined that the organization is authentic. In one embodiment, authentication of the organization and displaying of the success message occur when the first set of attributes matches the second set of attributes. Alternatively, GUI 700 is also configured to display a denial message (not shown) if it is determined that the organization is not authentic. In one aspect, authentication of the organization and displaying of the denial message occur when the first set of attributes does not match the second set of attributes. In another aspect, a graphical user interface (not shown) may comprise a display area configured to prompt the organization to provide additional patient-specific attributes. This may occur, for example, if the first set of attributes does not match the second set of attributes. Instead of displaying a denial message, the organization may be asked for additional attributes about the patient with which to compare to the information returned from the payor. If the additional attributes match the information returned from the payor, the organization may still be authenticated.

Figure 8:
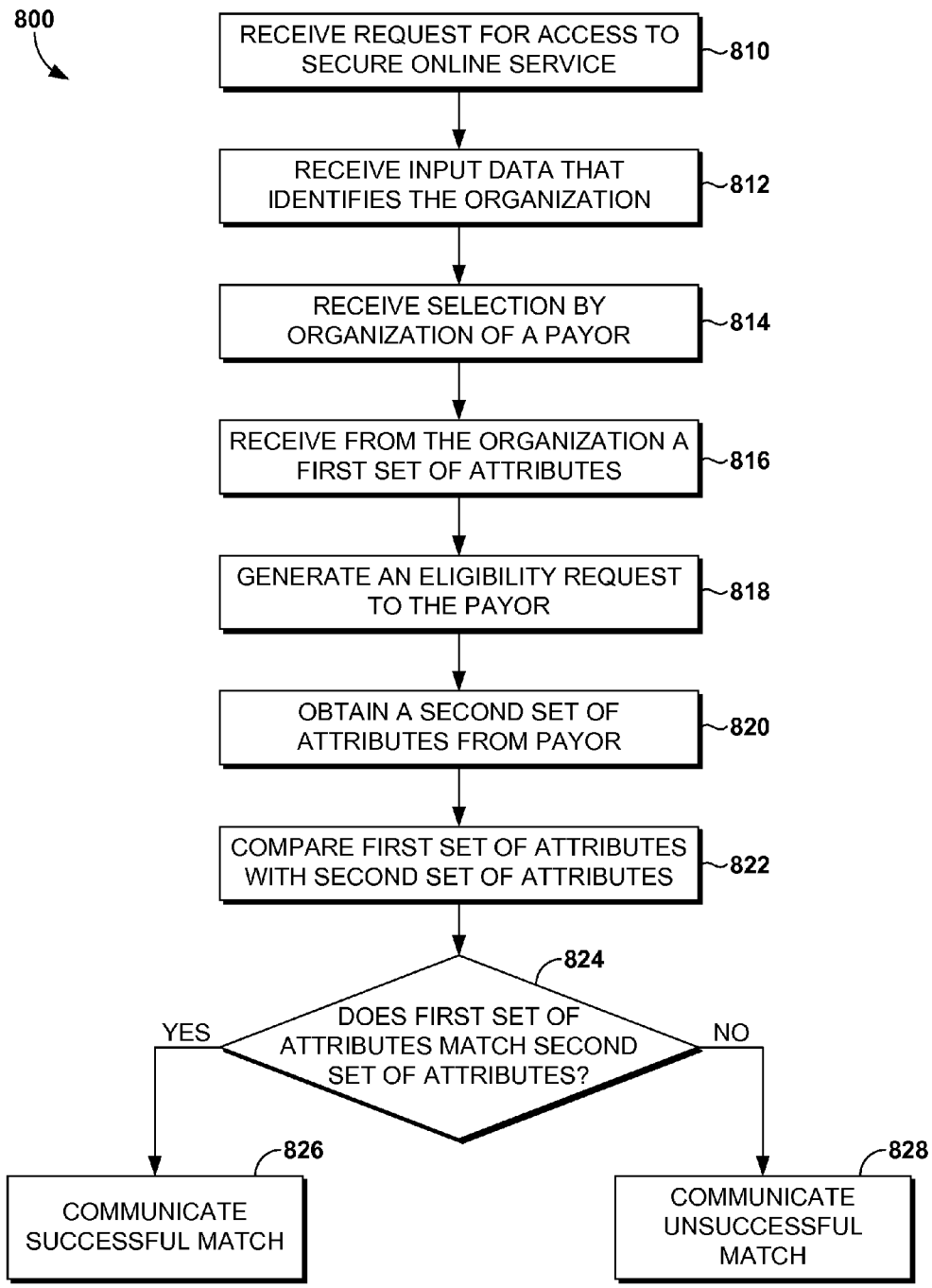
FIG. 8 is a flow diagram of a method in accordance with an embodiment of the present invention.

Turning to FIG. 8, an illustrative flow diagram 800 is shown of a method for online authentication of an organization using eligibility based criteria. Initially, a request is received from an organization for access to a secure online service provider at step 810. In one aspect, the secure online service provider is publicly accessible. In this case, the organization's initial encounter with the secure online service provider may be by accessing the welcoming screen of the secure online service provider as a result of a search query. In another aspect, the secure online service provider is not publicly accessible, and the organization's initial inquiry concerning cloud-based services may be through email or telephone. In such a case, the secure online service provider may issue an invitation to the organization to visit the secure online service provider site.

At step 812, input data is received that identifies the organization. In one embodiment where the secure online service provider site is publicly accessible, the organization inputs identifying data such as the organization's name, and the National Provider Identifier (NPI). In another embodiment where the site is not publicly accessible and an invitation is issued to visit the site, the secure online service provider pre-populates the identifying data of the organization into the online authentication system obviating the need for the organization to input such data.

In step 814, the selection by the organization of a payor is received, wherein the selected payor is tied to a patient who recently received services at the organization. In one embodiment, the organization may select a payor of its choice; while in another embodiment, the organization is limited to selecting a payor from a pre-defined list. In yet another embodiment, the online authentication system may randomly select a payor that will be used. If the payor is not one utilized by the organization, the organization may request that the online authentication service randomly select another payor.

With respect to step 814, payors may comprise private insurance companies, employer sponsored programs, or state or federally sponsored insurance programs such as Medicaid and Medicare. In one embodiment, the online authentication system may limit the payor choice to that of a state or federally sponsored insurance program. This provides another level of security because government sponsored programs require that a provider signature be on file. Thus, for example, if a sham organization is able to input data specific to a patient, it will still fail to be authenticated because there will not be a provider signature on file with the government sponsored program.

Still further with respect to step 814, in one embodiment of the invention, the patient receiving services at the organization is seen by the organization within 24 hours prior to receiving the selection of the payor by the organization. In another embodiment, the length of time between when the patient was seen by the organization and receiving the selection of the payor by the organization may vary. This is seen most often when the payor selected is a state or federally sponsored insurance program, and the organization does not see patients that use this type of insurance on a daily basis.

Turning to step 816, a first set of attributes is received from the organization, where the first set of attributes comprises data from a standard eligibility transaction between the organization and the payor regarding the patient. In one embodiment, the eligibility transaction is a standard, Health Insurance Portability and Accountability Act (HIPPA) mandated ASC X12N 270/271 eligibility request and response transaction as outlined above.

In step 818, an eligibility request to the payor is generated. In one embodiment, the eligibility request is generated after the online authentication service receives permission from the organization to perform a standard eligibility transaction for the specified patient and payor.

In step 820, a standard eligibility transaction is run on the patient with the payor to obtain a second set of attributes specific to the patient. In one embodiment, the eligibility transaction is a standard, Health Insurance Portability and Accountability Act (HIPPA) mandated ASC X12N 270/271 eligibility request and response transaction as outlined above.

Turning to step 822, the first set of attributes is compared to the second set of attributes. At step 824, it is determined whether the first set of attributes matches the second set of attributes. If the data does not match at step 824, the online authentication system will notify the secure online service provider that the match was unsuccessful. But in one aspect, if the first set of attributes does not match the second set of attributes, the organization may be prompted to select another patient and repeat the process using the new patient. Or, as mentioned above, the organization may be prompted to provide additional attributes about the patient with which to compare to the information returned by the payor. Returning to step 824, if the first set of attributes does match the second set of attributes, the online authentication system will notify the secure online service provider that the match was successful at step 828, and the secure online service provider can then make the determination whether to allow the organization access to the services offered by the secure online service provider.

Many different arrangements of the various components depicted, as well as components not shown, are possible without departing from the scope of the claims below. Embodiments of our technology have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

The invention claimed is:

1. One or more non-transitory computer-readable media having computer-executable instructions embodied thereon, that, when executed, enable a secure online service provider to authenticate a healthcare organization desiring access to one or more services provided by the online service provider using standard eligibility request and eligibility response transactions, the method comprising:
at the secure online service provider:
receiving from the healthcare organization a request for access to the one or more services provided by the secure online service provider;
receiving from the healthcare organization data that identifies the organization;
receiving from the healthcare organization a selection of a payor, wherein the selected payor is associated with a recent encounter between a patient and the healthcare organization;
receiving from the healthcare organization a first set of attributes specific to the patient, the first set of attributes generated using data from a first standard eligibility request communicated from the healthcare organization to the payor regarding the patient and a first standard eligibility response communicated from the payor to the healthcare organization regarding the patient, wherein the first standard eligibility request comprises a first set of patient information and the first standard eligibility response comprises a second set of patient information, a portion of which is unrelated to the first set of patient information and is payor-specific;
using the first set of attributes, generating a second standard eligibility request that comprises the first set of patient information;
communicating the second standard eligibility request to the selected payor;
receiving from the selected payor a second standard eligibility response regarding the patient, the second standard eligibility response comprising the second set of patient information, the portion of which is unrelated to the first set of patient information and is payor-specific, wherein the second standard eligibility request and the second standard eligibility response comprise a second eligibility request/response transaction;
generating a second set of attributes specific to the patient using the second standard eligibility request/response transaction;
comparing the first set of attributes with the second set of attributes to determine if the first set of attributes matches the second set of attributes; and
providing a notification to the healthcare organization that authentication was successful when the first set of attributes matches the second set of attributes.

2. The media of claim 1, wherein the data that identifies the healthcare organization comprises the organization's name and the organization's National Provider Identifier.

3. The media of claim 1, wherein the selected payor is any payor utilized by the healthcare organization.

4. The media of claim 1, wherein the selected payor is selected from a predefined list.

5. The media of claim 1, wherein the selected payor is randomly assigned to the healthcare organization by the secure online service provider.

6. The media of claim 5, wherein when the selected payor randomly assigned to the healthcare organization by the secure online service provider is not one used by the healthcare organization, allowing the healthcare organization to request that another payor be randomly assigned.

7. The media of claim 1, further comprising:
limiting the payor choice to that of a state or federally sponsored insurance program.

8. The media of claim 1, wherein the encounter between the patient and the healthcare organization has occurred within 24 hours of receiving from the healthcare organization the selection of the payor.

9. The media of claim 1, wherein the first standard eligibility request/response transaction comprises a standard, Health Insurance Portability and Accountability Act (HIPPA) mandated ASC X12N 270/271 eligibility request and response transaction.

10. The media of claim 1, wherein the second standard eligibility request/response transaction comprises a standard, Health Insurance Portability and Accountability Act (HIPPA) mandated ASC X12N 270/271 eligibility request and response transaction.

11. The media of claim 1, wherein when the first set of attributes does not match the second set of attributes providing a notification to the healthcare organization that authentication was unsuccessful and allowing the healthcare organization to repeat the online authentication method of claim 1 using a new patient.

12. The media of claim 1, wherein when the first set of attributes does not match the second set of attributes, communicating a request to the healthcare organization that the healthcare organization provide an additional set of attributes with which to compare to the second set of attributes.

13. An online authentication system hosted by a secure online service provider for authenticating a healthcare organization desiring to access one or more services provided by the secure online service provider, the online authentication system hosted by the secure online service provider comprising:
- a computing device having one or more processors and one or more computer-storage media; and
- a data store coupled with the online authentication system, wherein the online authentication system:
  - receives identifying information from the healthcare organization and a first set of patient-specific attributes from the healthcare organization, the first set of patient-specific attributes generated using data from a first standard eligibility request communicated from the healthcare organization to the payor regarding the patient and a first standard eligibility response communicated from the payor to the healthcare organization regarding the patient, wherein the first standard eligibility request comprises a first set of patient information and the first standard eligibility response comprises a second set of patient information, a portion of which is unrelated to the first set of patient information and is payor-specific;
  - utilizes the first set of patient-specific attributes to generate a second eligibility request that comprises the first set of patient information;
  - communicates the second eligibility request to the payor;
  - receives a second eligibility response from the payor regarding the patient, the second standard eligibility response comprising the second set of patient information, the portion of which is unrelated to the first set of patient information and is payor-specific;
  - generates a second set of patient-specific attributes using the second eligibility request and the second eligibility response;
  - compares the first set of patient-specific attributes with the second set of patient-specific attributes to determine if they match; and
  - notifies the healthcare organization that authentication was successful if the first set of patient-specific attributes matches the second set of patient-specific attributes, and that authentication was unsuccessful if the first set of patient-specific attributes does not match the second set of patient-specific attributes.

14. The system of claim 13, wherein the healthcare organization identifying information is already known to the online authentication system.

* * * * *